United States Patent [19]

McCoy et al.

[11] 3,979,415

[45] Sept. 7, 1976

[54] METHOD OF PREPARATION OF SULFONATED, DIALKYL-SUBSTITUTED BENZODIOXOLES

[75] Inventors: David R. McCoy; Mahmond S. Kablaoui, both of Wappingers Falls, N.Y.

[73] Assignee: Texaco Inc., New York, N.Y.

[22] Filed: Apr. 28, 1975

[21] Appl. No.: 572,552

Related U.S. Application Data

[63] Continuation-in-part of Ser. No. 483,598, June 27, 1974, abandoned.

[52] U.S. Cl. .............................................. 260/340.5
[51] Int. Cl.[2] ......................................... C07D 317/46
[58] Field of Search ................................. 260/340.5

[56] References Cited
UNITED STATES PATENTS
2,755,218  7/1956  Beroza .......................... 260/340.5 R

*Primary Examiner*—Ethel G. Love
*Attorney, Agent, or Firm*—T. H. Whaley; C. G. Ries; James F. Young

[57] ABSTRACT

Method of preparing a sulfonated, dialkyl-substituted benzodioxole by reacting a 1,2-dihydroxybenzene with an aliphatic ketone containing 5 to 30 carbon atoms therein and under dehydrating conditions in the presence of an acidic catalyst at 50–150°C. for 1 to 5 hours, removing the formed ketal from the reaction product and sulfonating said ketal with fuming sulfuric acid to form said sulfonated ketal.

9 Claims, No Drawings

METHOD OF PREPARATION OF SULFONATED, DIALKYL-SUBSTITUTED BENZODIOXOLES

This application is a continuation-in-part application of our application Ser. No. 483,598, filed June 27, 1974, for "METHOD OF PREPARATION OF SULFONATED, DIALKYL-SUBSTITUTED BENZODIOXOLES", now abandoned.

The present invention is directed to the preparation of 1,2-dihydroxybenzene ketal sulfonates.

These materials have utility as dispersants in aqueous drilling fluids and also as surfactants in detergent compositions.

It is known that one can prepare 1,2-dihydroxybenzene ketals using low molecular weight ketones under dehydrating conditions. Further, that the resulting ketals can be reacted to effect ring substitution by chlorination, nitrogenation and the like. However, the preparation of such sulfonated ketals by conventional practice such as the use of concentrated $H_2SO_4$ and a dehydrating agent such as $P_2O_5$ or acetic anhydride has not been successful for the ketal dissociates under the acidic reaction conditions. The alternative synthesis of sulfonated catechol ketals in one step from sulfonated catechols and ketone fails to give any reaction under a variety of dehydrating conditions.

It has now been found that a sulfonated 1,2-dihydroxybenzene ketal, as hereinafter more fully described, can be prepared in good yields by a novel method which comprises reacting 1,2-dihydroxybenzene with an aliphatic ketone containing from 3 to about 30 carbon atoms under dehydrating conditions, and thereafter effecting sulfonation of the thus prepared ketal under specific conditions and employing a specific sulfonating agent.

The starting material to be used in the preparation of the ketal is a 1,2-dihydroxbenzene (catechol) or a substituted 1,2-dihydroxybenzene containing 1–3 alkyl groups of from 1 to 10 carbons each.

Representative 1,2-dihydroxybenzenes are 3-methylcatechol, 3,4-dimethylcatechol, 4-isobutylcatechol, 3-t-butylcatechol, 3,4-di-t-butylcatechol, 3-decylcatechol, 4-octylcatechol, and the like.

The ketone component used in the preparation of the ketal is an aliphatic ketone containing from 3 to about 30 atoms therein. Suitable ketones may be simple or mixed ketones of varying carbon number within the above range. Particularly preferred ketones are those containing from about 3 to 6 carbon atoms as well as those containing from 10 to about 15 carbon atoms. A particularly preferred group of ketones consists of those ketones containing from 10 to 15 carbon atoms therein and prepared by the dehydrogenation of the corresponding secondary alkanols obtained by the boric acid-catalyzed air oxidation of linear hydrocarbon mixtures.

Representative ketones include the following species: diethyl-, di-propyl-, dibutyl-, dipentyl-, dioctyl-, dinonyl-, didecyl-, and didodecyl-, as well as asymmetric ketones such as methyl nonyl-, ethyl undecyl-, including mixtures of asymmetric ketones.

For the ketalization reaction, ketone to 1,2-dihydroxylbenzene ratios of 5:1 to 1:2 may be employed. Ratios near 1:1 are preferred. The presence of an acidic catalyst in at least 0.1 mole percent concentration (based on 1,2-dihydroxybenzene) is necessary. The reaction may be carried out neat or in the presence of any inert solvent at temperatures between 50°–150°C. Water of reaction must be removed by either azeotropic distillation or use of a drying agent (molecular sieve or acid anhydride). Preferred conditions employing $P_2O_5$ as both catalyst and drying agent and use of refluxing benzene or xylene as the reaction medium. Reaction times of 1–5 hours are usual.

In the sulfonation step, it is necessary to employ fuming sulfuric acid and to maintain reaction times and temperatures between 1 to 15 minutes, 50° to 150°C. Desired reaction times and temperatures are 80°–100°C. for 3–5 minutes only. Ketal to fuming sulfuric acid mole ratios of 1:1 to 1:20 may be employed. Ratios between 1:5 to 1:10 are preferred.

While the sulfonation step can be carried out without maintaining a blanket of an inert gaseous material over the reactants, it is preferred that a blanket of an inert gas such as nitrogen or argon be used.

Following is a description by way of example of a method of carrying out the present invention.

EXAMPLE I

Eight grams each of a mixed $C_{12}$–$C_{13}$ ketone (average M.W. 185), the keto functionality randomly distributed along carbon chain, catechol, and phosphorus pentoxide, were charged to a 250ml round bottom flux flask along with 100ml toluene at room temperature and blanketed with nitrogen gas. The mixture was heated to reflux under nitrogen atmosphere while stirring with a magnetic stirrer. Reflux was continued for 5½ hours. After cooling liquid solvent was decanted from the cooled product. The reaction produced was taken up in ether and washed first with 10% aqueous sodium hydroxide, then with water. Removal of solvents from the organic layer gave 9.99 g. of the corresponding ketal showing no —OH or C=O adsorption in the infrared.

Into a 3-necked flask equipped with a mechanical stirrer, a condenser with drying tube, nitrogen inlet, a thermometer and a dropping funnel was charged 25.g of 20% fuming sulfuric acid. Five grams of the above prepared ketalized catechol were added slowly from the dropping funnel under a blanket of dry nitrogen atmosphere. The mixture was heated to 90°C for 5 minutes. After cooling to room temperature the resulting reaction mixture was then added dropwise to a 40% aq. sodium hydroxide solution containing excess sodium hydroxide (25.0g). Following removal of the water, the residue was extracted twice with cold methanol and once with cold ethanol to give 4.57g of product, identified as sodium salt of the monosulfonated ketalized catechol.

Evaluation of this compound in a Standard Launder-Ometer Test showed it to be a moderately effective detergent for it had detergency coeffecient of 72%, as compared to a 100% rating for the standard, a linear alkylbenzene sulfonate.

COMPARATIVE EXAMPLE A

Sulfonation of the ketalized catechol (Example I) with conc. sulfuric acid (97%) and acetic anhydride instead of fuming sulfuric acid as in Example I above failed to give the desired product. Instead, catechol sulfonate and the original ketone, cleavage products of the starting materials, were isolated.

COMPARATIVE EXAMPLES B–E INCLUSIVE

The following reaction mixtures were refluxed for 24 hours each under nitrogen atmosphere. (B) $C_{12}$–$C_{13}$ ketone (25.3g), sulfonated catechol (25.3g), and toluene (200ml); (C) as in Example (B) except that toluene (70ml) and dimethylformamide (70ml) was the solvent system; (D) as in Example C with the addition of p-toluenesulfonic acid (0.5g); (E) $C_{12}-C_{13}$ ketone (2.0g), sulfonated catechol (3.0g), xylene (20ml), and phosphorus pentoxide (2.0g). Azeotropic removal of water was attempted in procedures B–D inclusive.

In each of these examples only the starting materials were recovered.

EXAMPLE II

There was added to 275 g. 3-pentanone and 150 g. phosphorus pentoxide, 150 g. catechol slowly with cooling to 50°C. After the addition, the mixture was heated to 120°–150°C. for 1½ hours with stirring. Product extracted into ether (800 ml.), washed with 10% NaOH solution and water, and ether evaporated to obtain 88% yield of the corresponding ketal, as 2,2-Diethyl-1,3-benzodioxole, identified by NMR and IR spectral data.

202 grams of this compound was added to 528 ml. 20% fuming sulfuric acid over a 70 min. period, with stirring at 34°–45°C. while maintaining a blanket of nitrogen over the reactants. The resulting mixture was heated to 90°C. for 5 minutes and cooled. This cooled mixture was added to 2.5 liters 40% NaOH solution over a 2-hour period at 50°C. The bulk of the water was removed and the residue extracted with ethanol, which yielded (quantitatively) upon evaporation a solid identified by its %S, NMR spectrum, and solubility characteristics as the desired sodium sulfonate of the ketalized catechol.

The above prepared material was found to be a satisfactory drilling fluid dispersant in aqueous drilling fluids. Specific details of its dispersing activity are to be found in our copending patent application, Ser. No. 483,599, entitled "Drilling Fluid", filed June 27, 1974, and incorporated herein by reference now U.S. Pat. No. 3,920,560, issued Nov. 18, 1975.

We claim:
1. A method of preparing a sulfonated ketal of a 1,2-dihydroxybenzene which comprises reacting a 1,2-dihydroxybenzene with an aliphatic ketone containing from 5 to about 30 carbon atoms therein in the presence of phosphorous pentoxide as the acid catalyst and a drying agent selected from the group consisting of a molecular sieve and an acid anhydride at a temperature in the range of from 50° to 150°C., for a period of 1 to 5 hours, extracting the formed ketal from said reaction products, sulfonating said extracted ketal with fuming sulfuric acid in the mole ratio of 1 mole of said ketal to 5 to 10 moles of sulfuric acid at 50° to 150°C., for 1 to 15 minutes, cooling said resulting reaction mixture and recovering the formed reaction product therefrom.

2. Method as claimed in claim 1 wherein said 1,2-dihydroxybenzene is catechol.

3. Method as claimed in claim 1 wherein said ketone is a mixed $C_{12}-C_{13}$ aliphatic ketone.

4. Method as claimed in claim 1 wherein the mole ratio of said dihydroxybenzene to said ketone in the reaction mixture is 1 to 1.

5. Method as claimed in claim 1 wherein $P_2O_5$ is used as the catalyst and the drying agent.

6. Method as claimed in claim 1 wherein the ketalization reaction is carried out in the presence of toluene as an inert solvent.

7. Method as claimed in claim 1 wherein the sulfonation reaction is carried out at 80°–100°C for 3–5 minutes.

8. Method as claimed in claim 1 wherein the ketal to fuming sulfuric acid mole ratios are between 1:5 and 1:10.

9. Method as claimed in claim 1 wherein during sulfonation, a blanket of an inert gaseous material selected from the group consisting of nitrogen and argon is maintained over the reactants.

* * * * *

UNITED STATES PATENT AND TRADEMARK OFFICE
CERTIFICATE OF CORRECTION

PATENT NO. : 3,979,415
DATED : September 7, 1976
INVENTOR(S) : David R. McCoy and Mahmoud S. Kablaoui It is certified that error appears in the above—identified patent and that said Letters Patent are hereby corrected as shown below:

On the first page of the patent inventor's name was

"Mahmond S. Kablaoui"

should be

-- Mahmoud S. Kablaoui --.

Signed and Sealed this

Fourteenth Day of December 1976

[SEAL]

Attest:

RUTH C. MASON
*Attesting Officer*

C. MARSHALL DANN
*Commissioner of Patents and Trademarks*